United States Patent [19]

Andreee et al.

[11] Patent Number: 5,371,062

[45] Date of Patent: Dec. 6, 1994

[54] SUBSTITUTED AZINES

[75] Inventors: Roland Andreee; Mark W. Drewes, both of Langenfeld; Hans-Joachim Santel, Leverkusen; Klaus Lürssen; Robert R. Schmidt, both of Bergisch Gladbach, all of Germany

[73] Assignee: Bayer Aktiengesellschaft, Leverkusen, Germany

[21] Appl. No.: 41,650

[22] Filed: Apr. 1, 1993

[30] Foreign Application Priority Data

Apr. 7, 1992 [DE] Germany .............................. 4211610

[51] Int. Cl.$^5$ .................... A01N 43/54; C07D 239/60
[52] U.S. Cl. ..................... 504/243; 504/242; 544/301; 544/302; 544/303; 544/306; 544/300; 544/310; 544/311; 544/312; 544/313; 544/314; 544/316; 544/317; 544/318; 544/321; 544/324; 544/323; 544/327; 544/328; 544/329; 544/331; 544/332
[58] Field of Search ................. 504/242, 243; 544/300, 544/301, 311, 314, 318, 323, 329, 303

[56] References Cited

FOREIGN PATENT DOCUMENTS

| | | |
|---|---|---|
| 0008192 | 7/1979 | European Pat. Off. . |
| 0223406 | 10/1986 | European Pat. Off. . |
| 0249708 | 4/1987 | European Pat. Off. . |
| 0287079 | 4/1988 | European Pat. Off. . |
| 0321846 | 12/1988 | European Pat. Off. . |
| 0366494 | 3/1989 | European Pat. Off. . |
| 0336494 | 10/1989 | European Pat. Off. . |
| 0346789 | 12/1989 | European Pat. Off. . |
| 0374839 | 12/1989 | European Pat. Off. . |
| 0402751 | 12/1990 | European Pat. Off. . |
| 0459243 | 5/1991 | European Pat. Off. . |
| 0469711 | 2/1992 | European Pat. Off. . |
| 4030041 | 9/1990 | Germany . |

OTHER PUBLICATIONS

Murugesan et al, Chemical Abstracts, vol. 115:256 220u (1991).
J. F. W. McOmie, J. Chem. Soc., 1957, pp. 1830–1833.
Theophil Eicher, Synthesis, 1988, pp. 525–529.
Henry C. Koppel, J. Org. Chem. 1961, pp. 792–803.
Wada et al. Chemical Abstracts 110, 1989, p. 273. entry 130532a.
Wada et al. Chemical Abstracts 110, 1989, p. 754, entry 142853q.
Kijima et al, Chemical Abstracts 93, 1980, p. 722. entry 150268c.

*Primary Examiner*—John M. Ford
*Attorney, Agent, or Firm*—Sprung, Horn, Kramer & Woods

[57] ABSTRACT

The present invention relates to new substituted azines, of the general formula (I)

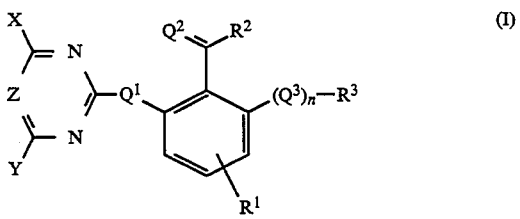

in which
n, $Q^1$, $Q^2$, $Q^3$, $R^1$, $R^2$, $R^3$, X, Y and Z have the meanings given in the description, to a plurality of processes for their preparation, and to their use as herbicides.

7 Claims, No Drawings

SUBSTITUTED AZINES

The invention relates to new substituted azines, to a plurality of processes for their preparation and to their use as herbicides.

A number of substituted azines having herbicidal properties have already been disclosed (compare JP-A 54117486 - cited in Chem. Abstracts 93, 150268c; EP-A 223,406; EP-A 249,708; JP-A 63258467 - cited in Chem. Abstracts 110, 130532a; JP-A 63258463 - cited in Chem. Abstracts 110, 192853q; EP-A 287,079; EP-A 374,839; EP-A 008,192; EP-A 321,846; EP-A 336,494; EP-A 459,243; DE-OS (German Published Specification) 4,030,041). Compounds from the publications mentioned, however, have until now attained no substantial importance.

The new substituted azines of the general formula (I) have now been found

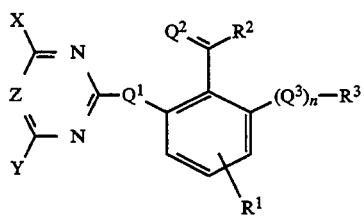   (I)

in which n represents the numbers 0 or 1, $Q^1$ and $Q^3$ are identical or different and represent oxygen, sulphur, NH or N-alkyl, $Q^2$ represents oxygen, sulphur or one of the groups below:

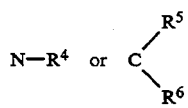

$R^1$ represents hydrogen, amino, hydroxyl, cyano, nitro, halogen or a radical of the series alkyl, halogenoalkyl, alkoxy, halogenoalkoxy, alkylthio, halogenoalkylthio, alkylamino, dialkylamino, alkylcarbonylamino, alkoxycarbonylamino, alkylsulphonylamino or phenyl, $R^2$ represents hydrogen, hydroxyl, alkyl or a radical, which is optionally substituted in each case, of the series alkoxy, alkylthio, alkylamino, dialkylamino, aralkyloxy, aralkylthio, aralkylamino, aryloxy, arylthio or arylamino, $R^3$ represents alkyl substituted by cyano, carboxyl or alkoxycarbonyl and having at least two carbon atoms, or alkenyl optionally substituted by cyano, carboxyl, halogen, alkoxycarbonyl, aryl (which is optionally substituted by halogen, alkyl or alkoxy) or heteroaryl, $R^4$ represents hydrogen, amino or a radical, which is in each case optionally substituted, of the series alkyl, alkenyl, alkinyl, aralkyl, aryl, alkoxycarbonyloxy, arylaminocarbonyloxy, carboxyalkoxy, alkoxycarbonylalkoxy, alkylamino, dialkylamino, aralkylamino, arylamino, N-alkyl-N-arylamino, alkylcarbonylamino, arylcarbonylamino, heteroarylamino, heteroarylcarbonylamino, alkoxycarbonylamino, alkylsulphonylamino or arylsulphonylamino, $R^5$ represents hydrogen, halogen, cyano, carboxyl, alkoxycarbonyl, alkylcarbonylamino or dialkoxyphosphoryl, $R^6$ represents formyl, cyano, carboxyl, hydroxymethyl, carbamoyl or a radical, which is in each case optionally substituted, of the series alkoxycarbonyl, cycloalkyloxycarbonyl, aralkoxycarbonyl, aryloxycarbonyl, heterocyclylalkoxycarbonyl, alkylthiocarbonyl, aralkylthiocarbonyl, arylthiocarbonyl, alkylaminocarbonyl, cycloalkylaminocarbonyl, aralkylaminocarbonyl, arylaminocarbonyl, dialkylaminocarbonyl, arylaminocarbonylalkoxycarbonyl, dialkylaminocarbonylalkoxycarbonyl, alkylaminocarbonylalkoxycarbonyl, alkylhydrazinocarbonyl, arylhydrazinocarbonyl, pyrrolidinylcarbonyl, piperidinylcarbonyl, morpholinylcarbonyl, piperazinylcarbonyl or phthalimidoxycarbonyl, X and Y are identical or different and represent hydrogen, halogen or a radical of the series alkyl, halogenoalkyl, alkoxy, halogenoalkoxy, alkylthio, alkylamino or dialkylamino and Z represents nitrogen or a CH— or C-halogen group.

The new substituted azines of the general formula (I) are obtained when (a) azine compounds of the general formula (II)

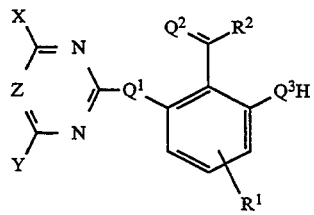   (II)

in which $Q^1$, $Q^2$, $Q^3$, $R^1$, $R^2$, X, Y and Z have the abovementioned meanings, are reacted with halogen compounds of the general formula (III)

$$X^1-R^3 \quad (III)$$

in which $R^3$ has the abovementioned meanings and $X^1$ represents halogen, if appropriate in the presence of an acid acceptor and if appropriate in the presence of a diluent, or when (b) benzene derivatives of the general formula (IV)

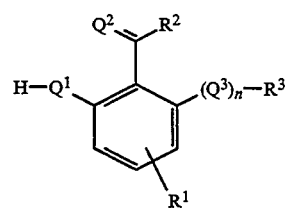   (IV)

in which n, $Q^1$, $Q^2$, $Q^3$, $R^1$, $R^2$ and $R^3$ have the abovementioned meanings, are reacted with reactive azines of the general formula (V)

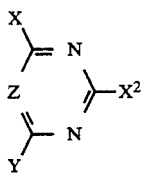 (V)

in which
X, Y and Z have the abovementioned meaning and
X² represents a nucleophilic leaving group, if appropriate in the presence of an acid acceptor and if appropriate in the presence of a diluent, or when (c) carbonyl compounds of the general formula (Ia)

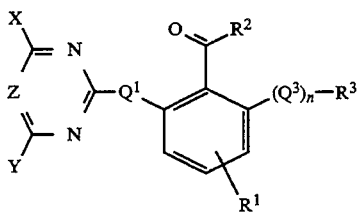 (Ia)

in which
n, $Q^1$, $Q^3$, $R^1$, $R^2$, $R^3$, X, Y and Z have the abovementioned meanings, are reacted with amino compounds of the general formula (VI)

 (VI)

in which
$R^4$ has the abovementioned meanings, or with methylene compounds of the general formula (VII)

 (VII)

in which
$R^5$ and $R^6$ have the abovementioned meanings, if appropriate in the presence of a reaction auxiliary and if appropriate in the presence of a diluent.

The new substituted azines of the general formula (I) are distinguished by potent herbicidal action.

The invention preferably relates to compounds of the formula (I), in which n represents the numbers 0 or 1, $Q^1$ and $Q^3$ are identical or different and represent oxygen, sulphur, NH or N—$C_1$–$C_4$-alkyl, $Q^2$ represents oxygen, sulphur or one of the groups below:

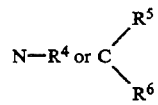

$R^1$ represents hydrogen, amino, hydroxyl, cyano, nitro, halogen or a radical of the series $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylamino, di-($C_1$–$C_4$-alkyl)amino, $C_1$–$C_4$-alkylcarbonylamino, $C_1$–$C_4$-alkoxy-carbonylamino, $C_1$–$C_4$-alkylsulphonylamino or phenyl, $R^2$ represents hydrogen, hydroxyl, $C_1$–$C_4$-alkyl or a radical, which is in each case optionally substituted, of the series $C_1$–$C_6$-alkoxy, $C_1$–$C_6$-alkylthio, $C_1$–$C_6$-alkylamino, di-($C_1$–$C_4$-alkyl)-amino, phenyl-$C_1$–$C_2$-alkyloxy, phenyl-$C_1$–$C_2$-alkylthio, phenyl-$C_1$–$C_2$-alkylamino, phenoxy, phenylthio or phenylamino, where the possible substituents in the alkyl moieties are preferably selected from the series fluorine, chlorine, cyano, nitro, carboxyl, $C_1$–$C_4$-alkoxy, $C_1$–$C_4$-alkoxy-carbonyl, and the possible substituents in the aryl moieties are preferably selected from the series fluorine, chlorine, bromine, cyano, nitro, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkoxycarbonyl, $R^3$ represents $C_2$–$C_6$-alkyl substituted by cyano, carboxyl or $C_1$–$C_4$-alkoxy-carbonyl or $C_2$–$C_6$-alkenyl optionally substituted by cyano, carboxyl, halogen, $C_1$–$C_4$-alkoxy-carbonyl, phenyl (which is optionally substituted by halogen, $C_1$–$C_4$-alkyl or $C_1$–$C_4$-alkoxy ), naphthyl, thienyl, furyl or pyridyl, $R^4$ represents hydrogen, amino or a radical, which is in each case optionally substituted by halogen, of the series $C_1$–$C_6$-alkyl, $C_3$–$C_6$-alkenyl, $C_3$–$C_6$-alkinyl, carboxy-$C_1$–$C_2$-alkoxy, $C_1$–$C_6$-alkoxycarbonyloxy, $C_1$–$C_4$-alkoxy-carbonyl-$C_1$–$C_2$-alkoxy, $C_1$–$C_6$-alkylamino, di-($C_1$–$C_2$-alkyl)-amino, $C_1$–$C_6$-alkyl-carbonylamino, $C_1$–$C_6$-alkoxycarbonylamino, $C_1$–$C_4$-alkyl-sulphonylamino, or phenyl, phenyl-$C_1$–$C_4$-alkyl, phenylaminocarbonyloxy, phenylamino, phenyl-$C_1$–$C_4$-alkylamino, N-($C_1$–$C_4$-alkyl)-phenylamino, pyridylamino, pyrimidylamino, pyridylcarbonylamino, phenylcarbonylamino, furylcarbonylamino, thienylcarbonylamino or phenylsulphonylamino in each case optionally substituted by nitro, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_4$-halogenoalkylthio, $C_1$–$C_4$-alkoxy-carbonyl and/or di-($C_1$–$C_2$-alkyl)-amino, $R^5$ represents hydrogen, halogen, cyano, carboxyl, $C_1$–$C_6$-alkoxy-carbonyl, $C_1$–$C_6$-alkylcarbonylamino or di-($C_1$–$C_4$-alkoxy)-phosphoryl, $R^6$ represents formyl, cyano, carboxyl, hydroxymethyl, carbamoyl or a radical, which is in each case optionally substituted by halogen, carboxyl or $C_1$–$C_4$-alkoxy-carbonyl, of the series $C_1$–$C_6$-alkoxy-carbonyl, $C_5$–$C_6$-cycloalkyloxycarbonyl, $C_1$–$C_6$-alkylthio-carbonyl, $C_1$–$C_6$-alkylamino-carbonyl, $C_5$–$C_6$-cycloalkylaminocarbonyl, di-($C_1$–$C_2$-alkyl)-amino-carbonyl, $C_1$–$C_4$-alkylaminocarbonyl-$C_1$–$C_4$-alkoxy-carbonyl, di-($C_1$–$C_2$-alkyl)-amino-carbonyl-$C_1$–$C_4$-alkoxycarbonyl, phenylaminocarbonyl-$C_1$–$C_4$-alkoxycarbonyl, N-methyl-phenylaminocarbonyl-$C_1$–$C_4$-alkoxy-carbonyl, or pyrrolidinylcarbonyl, piperidinylcarbonyl, morpholinylcarbonyl or piperazinylcarbonyl in each case optionally substituted by methyl and/or ethyl, or phenoxycarbonyl, phenyl-$C_1$–$C_4$-alkoxycarbonyl, furylmethoxycarbonyl, thienylmethoxycarbonyl, phenylthiocarbonyl, phenyl-$C_1$–$C_4$-alkylthiocarbonyl, phenylaminocarbonyl, phenyl-$C_4$–$C_4$-alkylamino-carbonyl, N-($C_1$–$C_4$- alkyl)-phenylamino-carbonyl or phenylhydrazinocarbonyl in each case optionally substituted by nitro, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxy-carbonyl and/or di-($C_1$–$C_2$-alkyl)-amino, or phthalimidoxycarbonyl, X and Y are identical or different and represent hydrogen, halogen or a radical of the series $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-alkylamino or di-($C_1$–$C_2$-alkyl)-amino and Z represents nitrogen or a CH or C-halogen group.

The aliphatic hydrocarbon radicals (for example alkyl, alkenyl, alkinyl) listed in the definition of the compounds according to the invention, also in combination with hetero atoms (for example in alkoxy, alkylthio, alkylamino), are in each case straight-chain or branched.

Halogen in each case in general represents fluorine, chlorine, bromine or iodine, preferably fluorine, chlorine or bromine, in particular fluorine or chlorine.

The invention relates in particular to compounds of the formula (I), in which n represents the numbers 0 or 1, $Q^1$ and $Q^3$ in each case represent oxygen, $Q^2$ represents oxygen or one of the groups below:

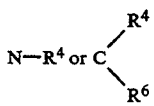

$R^1$ represents hydrogen, amino, hydroxyl, fluorine, chlorine, bromine, methyl, trifluoromethyl, methoxy, difluoromethoxy, trifluoromethoxy, methylthio, trifluoromethylthio, methylamino, dimethylamino, acetylamino, methoxycarbonylamino, methylsulphonylamino or phenyl, $R^2$ represents hydrogen, hydroxyl, methyl or methoxy, ethoxy, propoxy, butoxy, benzyloxy, phenylethoxy or phenoxy, each of which is optionally substituted, where the possible substituents in the alkyl moieties are preferably selected from the series comprising fluorine, chlorine, cyano, carboxyl, methoxy, ethoxy, methoxycarbonyl and ethoxycarbonyl, and the possible substituents in the aryl moieties are preferably selected from the series comprising fluorine, chlorine, bromine, methyl, trifluoromethyl, methoxy, trifluoromethoxy, methoxycarbonyl and ethoxycarbonyl, $R^3$ represents ethyl, propyl or butyl substituted by cyano, carboxyl, methoxycarbonyl or ethoxycarbonyl, or ethenyl, propenyl or butenyl optionally substituted by cyano, carboxyl, fluorine, chlorine, bromine, methoxycarbonyl, ethoxycarbonyl, phenyl (which is optionally substituted by fluorine, chlorine, bromine, methyl or methoxy), naphthyl, thienyl, furyl or pyridyl, $R^4$ represents hydrogen, amino, methyl, ethyl, propyl, isopropyl, butyl, isobutyl, sec-butyl, tert-butyl, allyl, propargyl, carboxymethoxy, carboxyethoxy, methoxycarbonyloxy, ethoxycarbonyloxy, propoxycarbonyloxy, butoxycarbonyloxy, methoxycarbonylmethoxy, ethoxycarbonylmethoxy, methoxycarbonylethoxy, ethoxycarbonylethoxy, methylamino, ethylamino, propylamino, isopropylamino, butylamino, isobutylamino, sec-butylamino, tert-butylamino, dimethylamino, acetylamino, propionylamino, methoxycarbonylamino, ethoxycarbonylamino, methylsulphonylamino, ethylsulphonylamino, or phenyl, benzyl, phenylaminocarbonyloxy, phenylamino, benzylamino, N-methyl-phenylamino, pyridylamino, pyrimidylamino, pyridylcarbonylamino, phenylcarbonylamino, furylcarbonylamino, thienylcarbonylamino or phenylsulphonylamino in each case optionally substituted by nitro, cyano, fluorine, chlorine, bromine, methyl, trifluoromethyl, methoxy, trifluoromethoxy, methylthio or trifluoromethylthio, $R^5$ represents hydrogen, fluorine, chlorine, cyano, carboxyl, $C_1$–$C_4$-alkoxy-carbonyl, $C_1$–$C_4$-alkylcarbonylamino, dimethoxyphosphoryl or diethoxyphosphoryl, $R^6$ represents formyl, cyano, carboxyl, hydroxymethyl, carbamoyl, or a radical of the series $C_1$–$C_4$-alkoxy-carbonyl, $C_5$–$C_6$-cycloalkyloxycarbonyl, $C_1$–$C_4$-alkylthiocarbonyl, $C_1$–$C_4$-alkylamino-carbonyl, $C_5$–$C_6$-cycloalkylamino-carbonyl, dimethylaminocarbonyl or $C_1$–$C_4$-alkylaminocarbonyl-$C_1$–$C_4$-alkoxy-carbonyl in each case optionally substituted by fluorine, chlorine, carboxyl or $C_1$–$C_4$-alkoxycarbonyl, or dimethylaminocarbonyl-$C_1$–$C_4$-alkoxy-carbonyl, or N-methylphenylaminocarbonyl-$C_1$–$C_4$-alkoxycarbonyl, or pyrrolidinyl-carbonyl, piperidinyl-carbonyl, morpholinyl-carbonyl or piperazinyl-carbonyl in each case optionally substituted by methyl and/or ethyl, or phenoxycarbonyl, benzyloxycarbonyl, phenylthiocarbonyl, benzylthiocarbonyl, phenylaminocarbonyl, benzylaminocarbonyl, N-methylphenylaminocarbonyl or phenylhydrazinocarbonyl in each case optionally substituted by nitro, cyano, fluorine, chlorine, bromine, methyl, trifluoromethyl, methoxy, trifluoromethoxy, methylthio or trifluoromethylthio, or phthalimidoxycarbonyl, X and Y are identical or different and represent hydrogen, chlorine, methyl, ethyl, trifluoromethyl, methoxy, ethoxy, difluoromethoxy, methylthio, methylamino, ethylamino or dimethylamino and Z represents nitrogen or a CH group.

If the starting substances used for process (a) according to the invention are, for example, 2-hydroxy-6-(4,6-dimethoxy-pyrimidin-2-yl-oxy)-benzaldehyde and β-chloropropionitrile, the course of the reaction can be represented by the following reaction scheme:

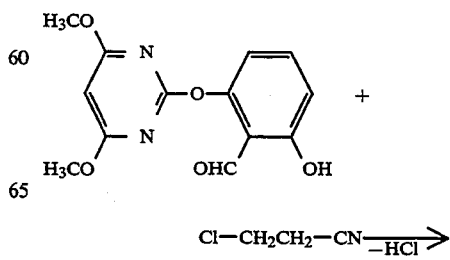

-continued

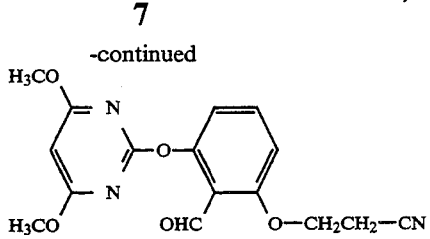

If the starting substances used for process (b) according to the invention are, for example, ethyl 2-hydroxy-6-styryl-benzoate and 2-chloro-4,6-dimethoxy-s-triazine, the course of the reaction can be represented by the following reaction scheme:

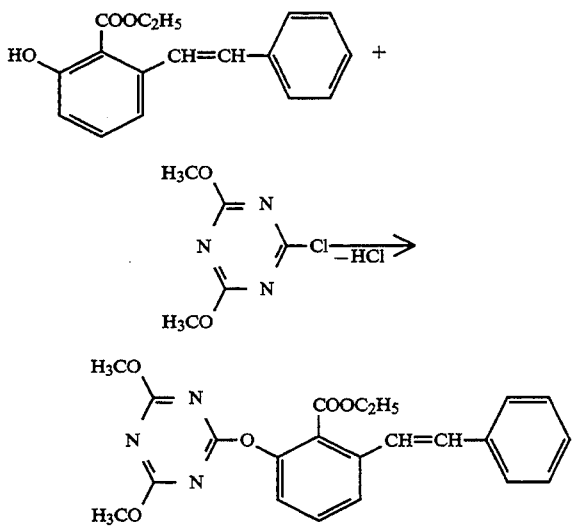

If the starting substances used for process (c) according to the invention are, for example, 2-(1-methoxycarbonyl ethoxy)-6-(4,6-dimethoxy-pyrimidin-2-yl-oxy)-acetophenone and methanesulphonic hydrazide, the course of the reaction can be represented by the following reaction scheme:

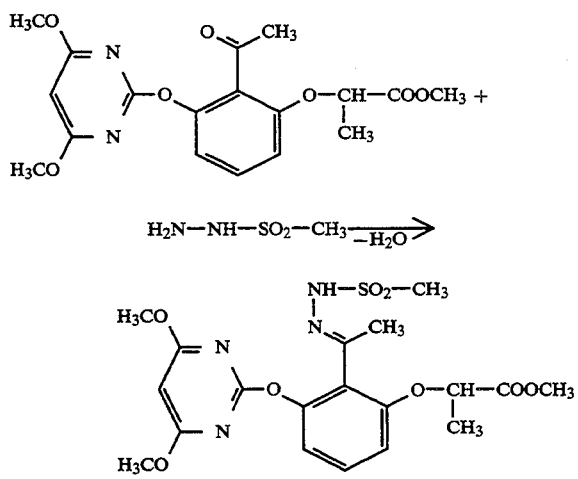

Formula (II) provides a general definition of the azine compounds to be used as starting substances for the preparation of compounds of the formula (I) in process (a) according to the invention.

In formula (II), $Q^1$, $Q^2$, $Q^3$, $R^1$, $R^2$, X, Y and Z preferably or in particular have those meanings which have already been given as preferred or as particularly preferred for $Q^1$, $Q^2$, $Q^3$, $R^1$, $R^2$, X, Y and Z in connection with the description of the compounds of the formula (I) according to the invention.

Examples of the starting substances of the formula (II) which may be mentioned are: 2-hydroxy-6-(4,6-dimethoxy-pyrimidin-2-yl-oxy)-benzaldehyde, 2-hydroxy-6-(4,6-dimethoxy-pyrimidin-2-yl-oxy)-benzoic acid, methyl 2-hydroxy-6-(4,6-dimethoxy-pyrimidin-2-yl-oxy)-benzoate and ethyl 2-hydroxy-6-(4,6-dimethoxy-pyrimidin-2-yl-oxy)-benzoate.

The starting substances of the formula (II) are known and/or can be prepared by processes known per se (cf. EP-A 249,708, EP-A- 321,846, EP-A 336,494, DE-OS (German Published Specification) 4,030,041).

Formula (III) provides a general definition of the halogen compounds additionally to be used as starting substances in process (a) according to the invention.

In formula (III), $R^3$ preferably or in particular has that meaning which has already been given for $R^3$ as preferred or as particularly preferred in connection with the description of the compounds of the formula (I) according to the invention; $X^1$ preferably represents chlorine, bromine or iodine.

Examples of the starting substances of the formula (III) which may be mentioned are:

β-chloro-(or bromo-)-propionitrile, γ-chloro-(or bromo-)butyronitrile, α- and β-chloro-(or bromo-)-propionic acid and their methyl esters and ethyl esters, α-, β- and γ-chloro-(or bromo-)-butyric acid and their methyl esters and ethyl esters.

The starting substances of the formula (III) are known chemicals for organic synthesis.

Process (a) according to the invention for preparing the new compounds of the formula (I) is preferably carried out using diluents. Suitable diluents here are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylene sulphone and hexamethylphosphoramide.

Acid acceptors which can be employed in process (a) according to the invention are all acid-binding agents customarily utilisable for reactions of this type. Those preferably suitable are alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium tert-butoxide and potassium tert-butoxide, and also aliphatic, aromatic or heterocyclic amines, for example triethylamine, trimethylamine, dimethylaniline, dimethylbenzylamine, pyridine, 1,5-diazabicyclo-[4.3.0]-non-5-ene (DBN), 1,8-diazabicyclo-[5.4.0]- undec-7-ene (DBU) and 1,4-diazabicyclo-[2.2.2]-octane (DABCO).

The reaction temperatures can be varied within a substantial range in process (a) according to the invention. In general, the reaction is carried out at temperatures between 0° C. and 150° C., preferably at temperatures between 20° C. and 100° C.

Process (a) according to the invention is in general carried out under normal pressure. However, it is also possible to work at elevated or reduced pressure.

To carry out process (a) according to the invention, the starting substances required in each case are in general employed in approximately equimolar amounts. However, it is also possible to use one of the two components employed in each case in a substantial excess. The reactions are in general carried out in a suitable diluent in the presence of an acid acceptor, and the reaction mixture is stirred for several hours at the temperature required in each case. Working-up is carried out in process (a) according to the invention in each case by customary methods (cf. the preparation examples).

Formula (IV) provides a general definition of the benzene derivatives to be used as starting substances in process (b) according to the invention for the preparation of compounds of the formula (I).

In formula (IV) n, $Q^1$, $Q^2$, $Q^3$, $R^1$, $R^2$ and $R^3$ preferably or in particular have those meanings which have been given as preferred or as particularly preferred for n, $Q^1$, $Q^2$, $Q^3$, $R^1$, $R^2$ and $R^3$ in connection with the description of the compounds of the formula (I) according to the invention.

Examples of the starting substances of the formula (IV) which may be mentioned are:

2-hydroxy-6-styryl-benzaldehyde and -benzoic acid and their methyl ester and ethyl ester.

The starting substances of the formula (IV) are known and/or can be prepared by processes known per se (cf. Synthesis 1988, 525–529).

Formula (V) provides a general definition of the reactive azines to be used additionally as starting substances in process (b) according to the invention.

In formula (V) X, Y and Z preferably or in particular have those meanings which have already been given above as preferred or as particularly preferred for X, Y and Z in connection with the description of the compounds of the formula (I) according to the invention;

$X^2$ preferably represents fluorine, chlorine, bromine or $C_1$–$C_4$-alkylsulphonyl, in particular chlorine or methylsulphonyl.

Examples of the starting substances of the formula (V) which may be mentioned are:

2-chloro- and 2-methylsulphonyl-4,6-dimethyl-pyrimidine, -4-methyl-6-methoxy-pyrimidine, -4,6-dimethoxy-pyrimidine, -4-methyl-6-ethoxy-pyrimidine, -4-chloro-6-methoxy-pyrimidine, -4-methyl-pyrimidine, -4-chloro-6-methyl-pyrimidine, -4-trifluoromethyl-6-methoxy-pyrimidine, -4-methoxy-6-difluoromethoxy-pyrimidine, -4-methyl-6-difluoromethoxy-pyrimidine, -4,6-bis-di-fluoromethoxy-pyrimidine, -4-chloro-6-ethoxy-pyrimidine, -4,6-diethoxy-pyrimidine, -4,5-dichloro-6-methyl-pyrimidine, -4-methyl-5-chloro-6-methoxy-pyrimidine, -4,6-dichloro-pyrimidine, -4-ethyl-6-methoxy-pyrimidine, -5-chloro-4,6-dimethoxy-pyrimidine, -4-methoxy-6-methylamino-pyrimidine and-4,6-bis-trifluoromethyl-pyrimidine, 2-chloro-4,6-dimethyl-s-triazine, -4-methoxy-6-methyl-s-triazine, -4,6-dimethoxy-s-triazine, -4-ethoxy-6-methyl-s-triazine and -4-ethyl-6-methoxy-s-triazine.

The reactive azines of the formula (V) are known and/or can be prepared by processes known per se (cf. J. Chem. Soc. 1957, 1830, 1833; J. Org. Chem. 26 (1961), 792; U.S. Pat. No. 3,308,119; U.S. Pat. 4,711,959).

Process (b) according to the invention is preferably carried out using a diluent. Suitable diluents in this case are the same diluents which have been given above for process (a) according to the invention.

Process (b) according to the invention is preferably carried out using an acid acceptor. Those suitable in this case are the same acid acceptors which have been given above for process (a) according to the invention.

The reaction temperatures in process (b) according to the invention can be varied within a substantial range. In general, the reaction is carried out at temperatures between 0° C. and 150° C., preferably at temperatures between 20° C. and 100° C.

Process (b) according to the invention is in general carried out under normal pressure. However, it is also possible to work at elevated or reduced pressure.

To carry out process (b) according to the invention, the starting substances required in each case are in general employed in approximately equimolar amounts. However, it is also possible to use one of the two components employed in each case in a substantial excess. The reactions are in general carried out in a suitable diluent in the presence of an acid acceptor, and the reaction mixture is stirred for several hours at the temperature required in each case. Working-up is carried out in process (b) according to the invention in each case by customary methods (cf. the preparation examples).

Formula (Ia) provides a general definition of the carbonyl compounds to be used as starting substances in process (c) according to the invention for the preparation of compounds of the formula (I).

In formula (Ia), n, $Q^1$, $Q^3$, $R^1$, $R^2$, $R^3$, X, Y and Z preferably or in particular have those meanings which have already been given above as preferred or as particularly preferred for n, $Q^1$, $Q^3$, $R^1$, $R^2$, $R^3$, X, Y and Z in connection with the description of compounds of the formula (I) according to the invention.

Examples of the starting substances of the formula (Ia) which may be mentioned are:

2-(2-cyano-ethoxy)-, 2-(3-cyano-propoxy)-, 2-(1-carboxyethoxy)-, 2-(2-carboxy-ethoxy)-, 2-(1-carboxy-propoxy)-, 2-(2-carboxy-propoxy)-, 2-(3-carboxy-propoxy)-, 2-(1-methoxycarbonyl-ethoxy)-, 2-(2-methoxycarbonyl-ethoxy)-, 2-(1-methoxycarbonyl-propoxy)-, 2-(2-methoxycarbonyl-propoxy)- and 2-(3-methoxycarbonyl-propoxy- -6-(4,6-dimethoxy-pyrimidin-2-yl-oxy)-benzaldehyde.

The starting substances of the formula (Ia) are new compounds according to the invention; they can be prepared by processes (a) or (b) according to the invention.

Formulae (VI) and (VII) provide a general definition of the amino compounds or methylene compounds additionally to be used as starting substances in process (c) according to the invention. In these formulae, $R^4$, $R^5$ and $R^6$ preferably or in particular have that meaning which has already been given as preferred or as particularly preferred for $R^4$, $R^5$ and $R^6$ in connection with the description of the compounds of the formula (I) according to the invention.

Examples of the starting substances of the formulae (VI) and (VII) which may be mentioned are:

ammonia, hydroxylamine, hydrazine, methylamine, ethylamine, propylamine, isopropylamine, butylamine, isobutylamine, sec-butylamine, tert-butylamine, allylamine, propargylamine, O-methyl-, O-ethyl-, O-propyl-, O-isopropyl-, O-butyl-, O-isobutyl- and O-sec-butylhydroxylamine, O-allylhydroxylamine, methyl and ethyl aminooxyacetate, methyl and ethyl α-aminooxy-propionate, methylhydrazine, ethylhydrazine, propylhydrazine, isopropylhydrazine, butylhydrazine, isobutylhydrazine, secbutyl-hydrazine, tert-butylhydrazine, N,N-dimethylhydrazine, acetohydrazide, propionylhydrazide, methoxycarbonylhydrazine, ethoxycarbonylhydrazine, methylsulphonylhydrazine, ethylsulphonylhydrazine, phenylhydrazine, benzoylhydrazine, benzenesulphonic hydrazide, p-toluenesulphonic hydrazide, malonic acid, cyanoacetic acid, malononitrile, methyl and ethyl cyanoacetate, dimethyl and diethyl malonate, γ-butyrolactone.

The starting substances of the formulae (VI) and (VII) are known chemicals for synthesis.

Process (c) according to the invention is preferably carried out using a diluent. Those suitable in this case are the same diluents which have already been given above for process (a) according to the invention.

Process (c) according to the invention is optionally carried out in the presence of a reaction auxiliary. Suitable reaction auxiliaries are substances which are customarily used to control and/or accelerate condensation reactions between carbonyl compounds and amino or methylene compounds. These include, in particular, basic compounds, such as, for example, sodium acetate, ammonium acetate, β-alanine, pyridine and piperidine.

The reaction temperatures in the process (c) according to the invention can be varied within a substantial range.

In general, the reaction is carried out at temperatures between 0° C. and 150° C., preferably at temperatures between 10° C. and 120° C.

Process (c) according to the invention is in general carried out under normal pressure. However, it is also possible to work at elevated or reduced pressure.

To carry out process (c) according to the invention, the starting substances required in each case are in general employed in approximately equimolar amounts. However, it is also possible to use one of the two components employed in each case in a substantial excess. The reactions are in general carried out in a suitable diluent, if appropriate in the presence of a reaction auxiliary, and the reaction mixture is stirred for several hours at the temperature required in each case. Working-up in the process according to the invention is in each case carried out by customary methods (compare the preparation examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea. Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture land, and for the selective combating of weeds in annual cultures.

The compounds of the formula (I) according to the invention are suitable for combating weeds pre-emergence and post-emergence.

To a certain extent, they also exhibit fungicidal action, for example against *Pyricularia oryzae.*

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

Example 1

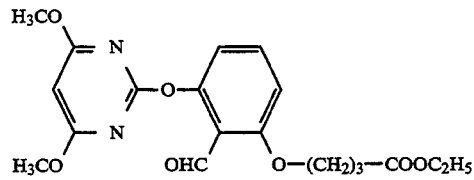

(Process (a))

A mixture of 1.66 g (6 mmol) of 2-hydroxy-6-(4,6-dimethoxy-pyrimidin-2-yl-oxy)-benzaldehyde, 1.17 g (6 mmol) of ethyl γ-bromo-butyrate, 2.1 g (15 mmol) of potassium carbonate and 50 ml of acetonitrile is heated under reflux for 8 hours and then concentrated in vacuo. The residue is shaken with ethyl acetate/water, and the organic phase is washed with saturated sodium hydrogen carbonate solution, dried with sodium sulphate and filtered. The filtrate is concentrated in vacuo, the residue is digested with diethyl ether and the crystalline product is isolated by filtering off with suction.

1.2 g (51% of theory) of 2-(3-ethoxycarbonyl-propoxy)-6-(4,6-dimethoxy-pyrimidin-2-yl-oxy)-benzaldehyde of melting point 96° C. are obtained.

Example 2

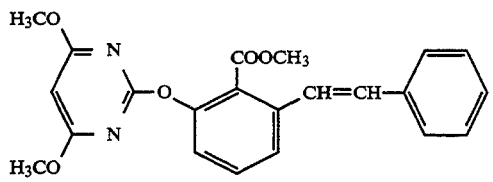

(Process b))

A mixture of 1.2 g (4.7 mmol) of methyl 2-hydroxy-6-styrylbenzoate, 1.02 g (4.7 mmol) of 4,6-dimethoxy-2-methylsulphonyl-pyrimidine, 0.8 g (5.7 mmol) of potassium carbonate and 50 ml of acetonitrile is heated under reflux for 15 hours and then concentrated. The residue is shaken with methylene chloride/water, and the organic phase is dried with sodium sulphate and filtered. The filtrate is concentrated and the residue is purified by column chromatography (silica gel; hexane/ethyl acetate, 10:1). 1.0 g (54% of theory) of methyl 2-styryl-6-(4,6-di-methoxy-pyrimidin-2-yl-oxy)-benzoate is obtained as an amorphous product.

Example 3

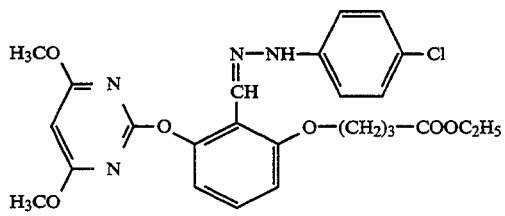

(Process (c))

A mixture of 2.93 g (7.5 mmol) of 2-(3-ethoxycarbonyl-propoxy)-6-(4,6-dimethoxy-pyrimidin-2-yl-oxy)-benzaldehyde (cf. Example 1), 1.5 g (8.3 mmol) of 4-chloro-phenylhydrazine-hydrochloride, 0.76 g (9.3 mmol) of sodium acetate and 150 ml of methylene chloride is stirred at 20° C. for 15 hours, then washed with saturated disodium hydrogen phosphate solution, dried with sodium sulphate and filtered. The filtrate is concentrated, the residue is stirred with methanol and the crystalline product is isolated by filtering off with suction. 2.6 g (67% of theory) of 2-(3-ethoxycarbonyl-propoxy)-6-(4,6-dimethoxy-pyrimidin-2-yl-oxy)-benzaldehyde-4-chloro-phenylhydrazone of melting point 139° C. are obtained.

The compounds of the formula (I)

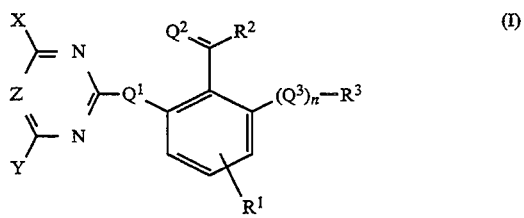

shown in Table 1 below can also be prepared, for example, analogously to Examples 1 to 3 and corresponding to the general description of the preparation process according to the invention.

TABLE 1

Examples of the compounds of the formula (I)

| Ex. No. | n | $Q^1$ | $Q^2$ | $Q^3$ | $R^1$ | $R^2$ | $R^3$ | X | Y | Z | Melting point (°C.) |
|---|---|---|---|---|---|---|---|---|---|---|---|
| 4 | 1 | 0 | N—NH—⌬—Cl | 0 | H | H | —CH(CH$_3$)COOCH$_3$ | OCH$_3$ | OCH$_3$ | CH | 158 |
| 5 | 0 | 0 | 0 | — | (3-)Br | OH | —CH=CH—⌬ | OCH$_3$ | OCH$_3$ | CH |  |
| 6 | 0 | 0 | 0 | — | H | OH | —CH=CH—⌬ | OCH$_3$ | OCH$_3$ | CH |  |
| 7 | 0 | 0 | 0 | — | H | OH | —CH=CH—⌬—Cl | OCH$_3$ | OCH$_3$ | CH | 128 |
| 8 | 0 | 0 | 0 | — | H | OCH$_3$ | —CH=CH—(thienyl) | OCH$_3$ | OCH$_3$ | CH | 113 |

TABLE 1-continued

Examples of the compounds of the formula (I)

| Ex. No. | n | $Q^1$ | $Q^2$ | $Q^3$ | $R^1$ | $R^2$ | $R^3$ | X | Y | Z | Melting point (°C.) |
|---|---|---|---|---|---|---|---|---|---|---|---|
| 9 | 0 | 0 | 0 | | — | H | $OCH_3$ | 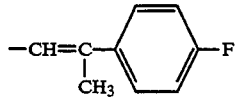 | $OCH_3$ | $OCH_3$ | CH | |
| 10 | 0 | 0 | 0 | | — | H | $OCH_3$ | 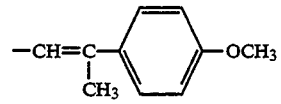 | $OCH_3$ | $OCH_3$ | CH | |
| 11 | 0 | 0 | 0 | | — | H | OH | 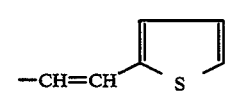 | $OCH_3$ | $OCH_3$ | CH | |
| 12 | 0 | 0 | 0 | | — | H | $OCH_3$ | 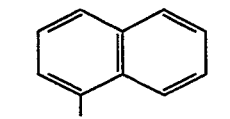 | $OCH_3$ | $OCH_3$ | CH | |
| 13 | 0 | 0 | 0 | | — | H | OH | 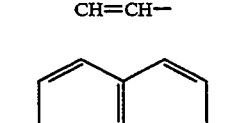 | $OCH_3$ | $OCH_3$ | CH | |
| 14 | 0 | 0 | 0 | | — | H | OH | 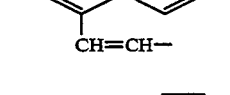 | $OCH_3$ | $OCH_3$ | CH | |

Example A

Pre-emergence test Solvent: 5 parts by weight of acetone Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example, the compounds according to Preparation Examples 2 and 6 exhibit a potent action against weeds.

Example B

Post-emergence test Solvent: 5 parts by weight of acetone Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. After three weeks, the degree of damage to the plants is rated in % damage in comparison to the development of the untreated control.

The figures denote:

0%=no action (like untreated control)
100%=total destruction

In this test, for example, the compounds according to Preparation Examples 2, 5 and 6 exhibit a potent action against weeds.

It will be understood that the specification and examples are illustrative but not limitative of the spirit and scope of the invention will suggest themselves to those skilled in the art.

What is claimed is:

1. A substituted azine of the formula

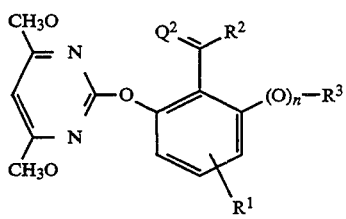

wherein n is 0 or 1, $Q^2$ is oxygen or

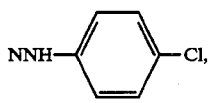

$R^1$ is hydrogen or halogen, $R^2$ is hydrogen, hydroxyl or methoxy, and $R^3$ is alkyl substituted by alkoxycarbonyl, or alkenyl substituted by aryl (which is optionally substituted by halogen, alkyl or alkoxy).

2. A herbicidal composition comprising a herbicidally effective amount of a compound according to claim 1 and a diluent.

3. A method of combating unwanted vegetation which comprises applying to such vegetation or to a locus from which it is desired to exclude such vegetation a herbicidally effective amount of a compound according to claim 1.

4. A compound according to claim 1, wherein such compound is 2-styryl-6-(4,6-dimethoxy-pyrimidin-2-yl-oxy)-methylbenzoate of the formula 5. A compound according to claim 1, wherein such compound is p1 3-bromo-2-styryl-6-(4,6-dimethoxy-pyrimidin-2-yl-oxy)-benzoic-acid of the formula

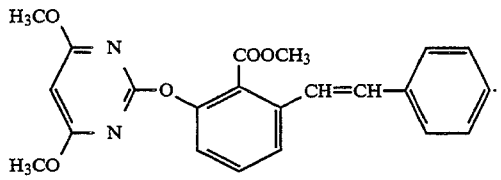

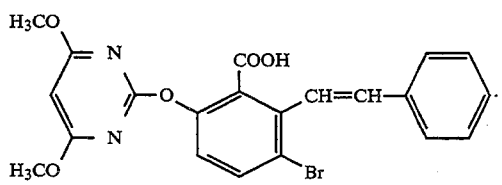

6. A compound according to claim 1, wherein such compound is
2-styryl-6-(4,6-dimethoxy-pyridin-2-yl-oxy)benzoic-acid of the formula

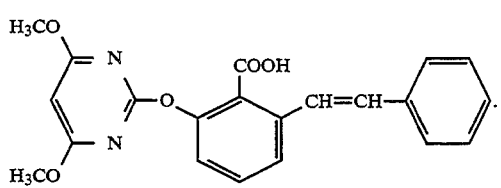

7. The method according to claim 3, wherein such compound is
2-styryl-6-(4,6-dimethoxy-pyridin-2-yl-oxy)-benzoic-acid,
2-styryl-6-(4,6-dimethoxy-pyrimidin-2-yl-oxy)-benzoic-acid;
2-styryl-6-(4,6-dimethoxy-pyrimidin-2-yl-oxy)-methylbenzoate.

* * * * *